US008673935B2

(12) United States Patent
Richard

(10) Patent No.: US 8,673,935 B2
(45) Date of Patent: *Mar. 18, 2014

(54) DRUGS FOR THE TREATMENT OF SARCOGYLCANOPATHIES

(75) Inventor: Isabelle Richard, Corbeil Essonnes (FR)

(73) Assignees: Genethon (FR); Centre National de la Recherche Scientifique (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/562,865

(22) Filed: Jul. 31, 2012

(65) Prior Publication Data

US 2013/0035353 A1 Feb. 7, 2013

Related U.S. Application Data

(63) Continuation of application No. 12/374,317, filed as application No. PCT/FR2007/001211 on Jul. 16, 2007, now Pat. No. 8,273,763.

(30) Foreign Application Priority Data

Jul. 18, 2006 (FR) ..................................... 06 53020

(51) Int. Cl.
*A61K 31/437* (2006.01)
*A61P 43/00* (2006.01)
*G01N 33/566* (2006.01)

(52) U.S. Cl.
USPC ........................... 514/300; 514/328; 435/7.21

(58) Field of Classification Search
USPC .................................. 514/300, 328; 435/7.21
See application file for complete search history.

(56) References Cited

FOREIGN PATENT DOCUMENTS

EP 1 618 881 A 1/2006

OTHER PUBLICATIONS

Katherine M. D. Bushby, Making sense of the limb-girdle muscular dytrophies, Brain (1999), vol. 122, pp. 1403-1420.*
International Search Report for PCT/FR2007/001211 dated Mar. 31, 2008.
Assereto, Stefania et al; "Pharmacological rescue of the dystrophin-glycoprotein complex in Duchenne and Becker skeletal muscle explants by proteasome inhibitor treatment"; American Journal of Physiology—Cell Physiology; Feb. 2006; pp. C577-C582; vol. 290, No. 2.
Bonuccelli, Gloria et al; "Proteasome Inhibitor (MG-132) Treatment of mdx Mice Rescues the Expression and Membrane Localization of Dystrophin and Dystrophin-Associated Proteins"; American Journal of Pathology; Oct. 2003; pp. 1663-1675; vol. 163, No. 4.
Mathews, Katherine D et al; "Limb-Girdle Muscular Dystrophy"; Current Neurology and Neuroscience Reports, Current Science, Philadelphia, PA; Jan. 2003; pp. 78-85; vol. 3, No. 1.
Kar N C et al; "Glycosidases in Normal and Diseased Human Muscle"; Clinica Chimica ACTA; 1973; pp. 269-271; vol. 45, No. 3.
Kawai, Hisaomi et al; "Lysosomal enzyme activities in skeletal muscle of patients with neuromuscular diseases"; Muscle and Nerve; 1995; pp. 1009-1015; vol. 18, No. 9.

* cited by examiner

*Primary Examiner* — Savitha Rao
*Assistant Examiner* — Angela Brown-Pettigrew
(74) *Attorney, Agent, or Firm* — Heslin Rothenberg Farley & Mesiti P.C.

(57) ABSTRACT

Inhibitors of the endoplasmic reticulum associated degradation (ERAD) pathway, particularly inhibitors of mannosidase I, are used for the preparation of a medicinal product intended to treat sarcoglycanopathies.

18 Claims, 6 Drawing Sheets

A/

αβγδ    R77Cβγδ    R77Cβγδ + dMJ: 100 μM

B/

αβγE262K    αβγE262K + dMJ 5μM    αβγE262K + dMJ 100μM

αβγE262K + dMJ 5μM

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Synthetic Primer

<400> SEQUENCE: 1
gcccaggtgg ctgtgctaca cacagcgca                                          29

<210> SEQ ID NO 2
<211> LENGTH: 29
<212> TYPE: DNA
<213> ORGANISM: Artificial Sequence
<220> FEATURE:
<223> OTHER INFORMATION: Synthetic Primer

<400> SEQUENCE: 2
tgcgctgtgt gtagcacagc cacctgggc                                          29

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
tataaccctg gcttcctcta                                                    20

<210> SEQ ID NO 4
<211> LENGTH: 24
<212> TYPE: DNA
<213> ORGANISM: Artificial Sequence
<220> FEATURE:
<223> OTHER INFORMATION: Synthetic Primer

<400> SEQUENCE: 4
cgaattcgcc aatgacaaga cgct                                               24

<210> SEQ ID NO 5
```

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
tagtggctca tgcctttaat                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
tgtgtttggg acttatgggg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
caatcagcag cagcagcctc                                              20

<210> SEQ ID NO 8
<211> LENGTH: 28
<212> TYPE: DNA
<213> ORGANISM: Artificial Sequence
<220> FEATURE:
<223> OTHER INFORMATION: Synthetic Primer

<400> SEQUENCE: 8
gccccggtgg ctctgctaca cccagcgc                                     28
```

DRUGS FOR THE TREATMENT OF SARCOGYLCANOPATHIES

CROSS REFERENCE TO RELATED APPLICATIONS

This application is a continuation of U.S. patent application Ser. No. 12/374,317, filed Mar. 25, 2009, which is a United States national stage filing under section 371 of International Application No. PCT/FR2007/001211 filed on Jul. 16, 2007, and published in French on Jan. 24, 2008 as WO 2008/009802 and claims priority of French application No. 0653020 filed on Jul. 18, 2006, the entire disclosure of these applications being hereby incorporated herein by reference.

TECHNICAL FIELD

This invention relates to the treatment of sarcoglycanopathies.

More precisely, the invention concerns the use of inhibitors of the endoplasmic reticulum associated degradation pathway, particularly mannosidase I inhibitors, as medicinal products intended for the treatment of certain forms of the disease.

PRIOR ART

Sarcoglycanopathies are autosomal recessive muscular disorders of the Limb Girdle Muscular Dystrophy (LGMD) group. Four forms of the disease have been identified (LGMD 2C, LGMD 2D, LGMD2E, and LGMD 2F), resulting respectively from defects in the γ-, α-, β- and δ-sarcoglycan genes (11, 17).

LGMD2C is particularly widespread in the Mediterranean basin and in Gypsy populations residing in Europe. LGMD2D has been diagnosed across the world in patients in Europe, Africa, Japan and Brazil. LGMD2E has been diagnosed for the most part in the Amish community and in North Africa. Until now, LGMD2F has only been reported in 7 families of Brazilian, Turkish and Italian origin.

Patients with sarcoglycanopathies present progressive muscular weakness of the pelvic and shoulder girdle muscles which is often associated with calf hypertrophy. Cognitive impairment is absent. Cardiac complications such as cardiomyopathies are sometimes observed in LGMD2C, LGMD2E and LGMD2F patients.

Upon histological examination, muscles show areas of regeneration and degeneration, inflammatory infiltrates, fibrosis and variation in fibre size. The severity of the disease is variable, even among siblings. In the most severe cases, patients lose the ability to walk before the age of 30 and their life expectancy is reduced.

Recurrent mutations occur in two forms of the disease. In LGMD2C patients, the del521T and C283Y mutations are frequently observed in North African and Gypsy populations, respectively (4, 13).

The most frequent mutation found in LGMD2D patients is the R77C substitution where the arginine in position 77 is replaced by a cysteine. One third of European patients carry this mutation, except in Finland where it is observed in 100% of patients, most often on both alleles (5, 9).

Sarcoglycans (SG) are a group of plasma membrane glycoproteins that associate with dystrophin to form the dystrophin glycoprotein complex (12). This complex contributes to the mechanical link between the actin cytoskeleton and the extracellular matrix and consequently plays a role in muscle fibre membrane stability (10). Sarcoglycans consist of a small intracellular domain that can be either C-terminal (α-sarcoglycan) or N-terminal (γ-, β- and δ-sarcoglycans), a single transmembrane domain and a large extracellular domain bearing N-glycosylation sites.

Sarcoglycan complex assembly occurs during transport of these proteins in the sarcoplasmic reticulum and the Golgi apparatus (6, 16). Assembly is initiated by β-sarcoglycan which binds to δ-sarcoglycan to position the complex correctly within the membrane. Then, α-sarcoglycan binds to the complex and in turn binds γ-sarcoglycan for complete assembly. Mutations in any sarcoglycan can disrupt assembly of the complex, causing secondary deficiency of the other sarcoglycans.

Whilst today we know how to diagnose sarcoglycanopathies, and even attribute the phenotype to specific mutations in the γ-, α-, β- or δ-sarcoglycans, we still have few options for treating patients with this disease.

Until now, no specific treatment has been developed and most patients require physiotherapy to avoid muscle cramps worsening. However, several teams have reported positive results in experiments using gene transfer via viral vectors or cell therapy in animal models (1, 7, 14). For this reason, document WO 00/20582 recommends use of a gene therapy approach to replace the defective sarcoglycan gene, in particular using AAV vectors.

In the prior art, an overall therapeutic approach, in which proteasome function was inhibited, was put forward for the treatment of muscular disorders, in particular muscular dystrophies. However, this non-specific approach does not seem to be particularly effective and could lead to tolerance problems.

It is therefore critical to develop new therapeutic approaches, in particular with new medicinal products that specifically and effectively treat sarcoglycanopathy patients

OBJECT OF THE INVENTION

This invention is based on results reported by the inventors demonstrating that:
- some sarcoglycan mutations associated with sarcoglycanopathies produce glycoproteins displaying defective folding;
- these misfolded proteins are disposed of via the endoplasmic reticulum associated glycoprotein degradation pathway;
- inhibitors of this pathway block defective sarcoglycan protein degradation;
- if not degraded (in the presence of inhibitors), defective sarcoglycans can be correctly translocated to the plasma membrane and assembled in the sarcoglycan complex, leading to recovery of a normal phenotype.

It should be recalled that endoplasmic reticulum (ER) glycosidases play an important role in controlling the quality of glycoprotein production. They ensure that only correctly folded glycoproteins are transported to their final location. In particular, cleavage of mannose residues in the ER by α-mannosidases acts as a signal guiding misfolded glycoproteins towards the proteasome for degradation.

α-mannosidases belong to two groups. Class I mannosidases (mannosidase I) are inhibited by 1-deoxymannojirimycin and kifunensin, while class II mannosidases are specifically inhibited by swainsonine. The proteasome is a protein complex involved in the degradation of intracellular proteins in the cytosol and can for example be inhibited by MG132 or bortezomib.

In theory any inhibitor of this degradation pathway (ERAD: Endoplasmic Reticulum Associated Degradation)

could be used. However, this invention has focused on mannosidase I inhibitors which have proved to have a very selective mode of action and are remarkably efficient for treating sarcoglycanopathies. From a clinical point of view, this notably corresponds to potentially lesser adverse effects.

Consequently, the invention relates to the use of class I α-mannosidase inhibitors for the preparation of a medicinal product intended to treat sarcoglycanopathies.

It is therefore clear that in the context of this invention, use of at least one mannosidase I inhibitor has been investigated. Naturally, the use of a "cocktail" of inhibitors is not rejected, namely several inhibitors of different types, with complementary inhibitory activities, particularly in regard to their activity/selectivity Kifunensin (CAS 109944-15-2) and 1-deoxymannojirimycin (CAS 84444-90-6) molecules are particularly preferred since they are known to inhibit mannosidase I.

However, the scope of this invention is not limited to these molecules. Indeed, any candidate molecule may be tested for its mannosidase I inhibitory activity using a simple enzymatic assay.

Considering that the aim of this approach is to find therapeutic solutions for human sarcoglycanopathies, the enzyme used for testing should be a class 1 alpha-mannosidase of human origin, particularly the enzyme referenced in databases under accession number: NP_005898 (mannosidase, alpha, class 1A, member 1 [*Homo sapiens*]).

An enzymatic assay suitable for testing such inhibitors was, for example, described in the article published in *J. Biol. Chem.* 2004 Oct. 8; 279(41):42638-47. Epub 2004 Jul. 22. *"The twisted abdomen phenotype of Drosophila POMT1 and POMT2 mutants coincides with their heterophilic protein O-mannosyltransferase activity"*, Ichimiya T, Manya H, Ohmae Y, Yoshida H, Takahashi K, Ueda R, Endo T, Nishihara S.

The method of administration, the dose administered, and the frequency of administration are determined for each specific case, using classic protocols known to those skilled in the art. These parameters depend particularly on the mutation to be treated and the inhibitor used.

Kifunensin is a preferable choice. This inhibitor is highly specific and has the advantage of being water-soluble and is therefore suitable for oral administration.

Besides, this method of treatment is particularly appropriate for treating sarcoglycanopathies caused by the human α-sarcoglycan R77C mutation (Arg77Cys in the protein corresponding to a 229C>T mutation on the gene). As previously discussed, this mutation is responsible for numerous clinical cases, especially in Europe.

However, the applicant has demonstrated that 1-deoxymannojirimycin can also be used instead of kifunensin.

In addition, in the context of this invention, it has been demonstrated that the effect observed is not specific to a particular mutation in a particular sub-unit.

In fact, the same beneficial effect was observed in the β- and δ-subunits, more precisely for the Q11E and E262K mutations respectively irrespective of the inhibitor used.

For this reason, this treatment may potentially be administered for disorders related to all known mutations in the four human sarcoglycans. However, only point mutations should be considered for this approach since truncated proteins caused by nonsense mutations or deletions will not, in theory, be active even if not degraded.

The main point mutations reported at the present time are listed in the Table I below. This list is not exhaustive.

TABLE I

| Exon | Nucleotide substitution | Amino acid substitution |
|---|---|---|
| α-sarcoglycan | | |
| 02 | c.92T > C | p.Leu31Pro |
| 02 | c.100C > T | p.Arg34Cys |
| 02 | c.101G > A | p.Arg34His |
| 03 | c.184T > C | p.Tyr62His |
| 03 | c.203G > A | p.Gly68Gln |
| 03 | c.220C > T | p.Arg74Trp |
| 03 | c.229C > T | p.Arg77Cys |
| 03 | c.266_267inv | p.Leu89Pro |
| 03 | c.269A > G | p.Tyr90Cys |
| 03 | c.271G > C | p.Gly91Arg |
| 03 | c.278C > T | p.Ala93Val |
| 03 | c.290A > G | p.Asp97Gly |
| 03 | c.292C > T | p.Arg98Cys |
| 03 | c.293G > A | p.Arg98His |
| 03 | c.308T > C | p.Ile103Thr |
| 04 | c.329G > T | p.Arg110Leu |
| 04 | c.371T > C | p.Ile124Thr |
| 05 | c.409G > A | p.Glu137Lys |
| 05 | c.421C > A | p.Arg141Ser |
| 05 | c.472C > T | p.Leu158Phe |
| 05 | c.518T > C | p.Leu173Pro[a] |
| 05 | c.524T > C | p.Val175Ala[a] |
| 05 | c.541C > T | p.Arg181Cys |
| 06 | c.586G > A | p.Val196Ile |
| 06 | c.614C > A | p.Pro205His |
| 06 | c.662G > A | p.Arg221His |
| 06 | c.683C > A | p.Pro228Gln |
| 06 | c.724G > T | p.Val242Phe |
| 06 | c.725T > C | p.Val242Ala |
| 06 | c.739G > A | p.Val247Met[a] |
| 07 | c.850C > T | p.Arg284Cys |
| β-sarcoglycan | | |
| 01 | c 31C > G | p Gln11Glu |
| 03 | c.265G > A | p.Val89Met |
| 03 | c.271C > T | p.Arg91Cys |
| 03 | c.272G > C | p.Arg91Pro |
| 03 | c.274_275AT > TC | p.Ile92Ser |
| 03 | c.275T > C | p.Ile92Thr |
| 03 | c.299T > A | p.Met100Lys |
| 03 | c.323T > G | p.Leu108Arg |
| 03 | c.341C > T | p.Ser114Phe |
| 03 | c.355A > T | p.Ile119Phe |
| 03 | c.416G > A | p.Gly139Asp |
| 04 | c.452C > G | p.Thr151Arg |
| 04 | c.499G > A | p.Gly167Ser |
| 04 | c.538T > C | p.Phe180Leu |
| 04 | c.544A > G | p.Thr182Ala |
| 04 | c.551A > G | p.Tyr184Cys |
| δ-sarcoglycan | | |
| 04 | c.212G > C | p.Arg71Thr |
| 06 | c.451T > G | p.Ser151Ala |
| 08 | c.593G > C | p.Arg198Pro |
| 08 | c.631A > T | p.Asn211Tyr |
| 09 | c.784C > A | p.Glu262Lys |
| γ-sarcoglycan | | |
| 03 | c.205G > C | p.Gly69Arg |
| 03 | c.206G > C | p.Gly69Asp |
| 03 | c.269T > C | p.Leu90Ser |
| 07 | c.581T > C | p.Leu194Ser |
| 07 | c.629A > G | p.His210Arg |
| 08 | c.787G > A | p.Glu263Lys |
| 08 | c.848G > A | p.Cys283Tyr |

A second aspect of the invention relates to the assay used for in vitro assessment of the efficacy of inhibitors of the endoplasmic reticulum associated degradation (ERAD) pathway, used for the treatment of sarcoglycanopathies. This assay consists of the following steps:

co-transfection of cells with the four sarcoglycan genes (γ-, α-, β- and δ-), of which one carries the mutation to be tested;

incubation for several hours in the presence of the inhibitor;

localisation of the sarcoglycan complex.

To advantage, human sarcoglycan genes carrying point mutations should be used.

If the complex is found to be located in the plasma membrane, then the inhibitor is identified as effective for the mutation being tested, and therefore can be considered for use in a therapeutic approach aiming to treat that specific form of sarcoglycanopathy.

Detection of the complex in the plasma membrane implies that:

firstly the inhibitor has prevented degradation of the defective protein;

and the mutant protein has translocated correctly and has integrated the plasma membrane complex.

To advantage, this procedure is undertaken in parallel on:

cells co-transfected with the four wild-type sarcoglycan genes: this is the positive control;

cells incubated in the same experimental conditions but without the inhibitor: this is the negative control and provides the basis for assessing the possible effects of the inhibitor.

Preferably, detection of the complex is performed by immunohistochemistry, using antibodies against at least one of the sarcoglycans.

Alternatively, one of the sarcoglycans can be tagged, notably using fluorescent tags, and then detected by microscopy or flow cytometry. This solution is advantageous compared to immunological techniques because it involves fewer experimental steps. However, it is important to check that the fusion protein (sarcoglycan+tag) does not disturb assembly of the complex.

In both cases, detection methods can, but do not necessarily, target the sarcoglycan carrying the mutation (choice of antibody or choice of sarcoglycan to be tagged).

It should be noted that this method for screening inhibitors may be used in vivo, in particular in transgenic mice bearing the relevant sarcoglycan mutation.

BRIEF DESCRIPTION OF THE DRAWINGS

The invention and the advantages that it presents are best demonstrated by the following series of experiments illustrated by the figures appended to this document. However, these experiments should not be considered to limit the scope of this invention.

The invention is mostly illustrated by experiments using an α-sarcoglycan protein carrying the R77C mutation in the presence of MG132 (proteasome inhibitor) and kifunensin (mannosidase I inhibitor).

B/Immunohistochemical labelling of δ-sarcoglycan in cells quadritransfected with the three α-, β- and γ-sarcoglycans and mutant E262K δ-sarcoglycan with or without 1-deoxymannojirimycin (dMJ) 5 or 100

C/Immunohistochemical labelling of β-sarcoglycan in cells quadritransfected with the three α-, γ- and δ-sarcoglycans and mutant Q11E β-sarcoglycan with or without 1-deoxymannojirimycin (dMJ) 5, 50 or 100 μM.

Figure 13:
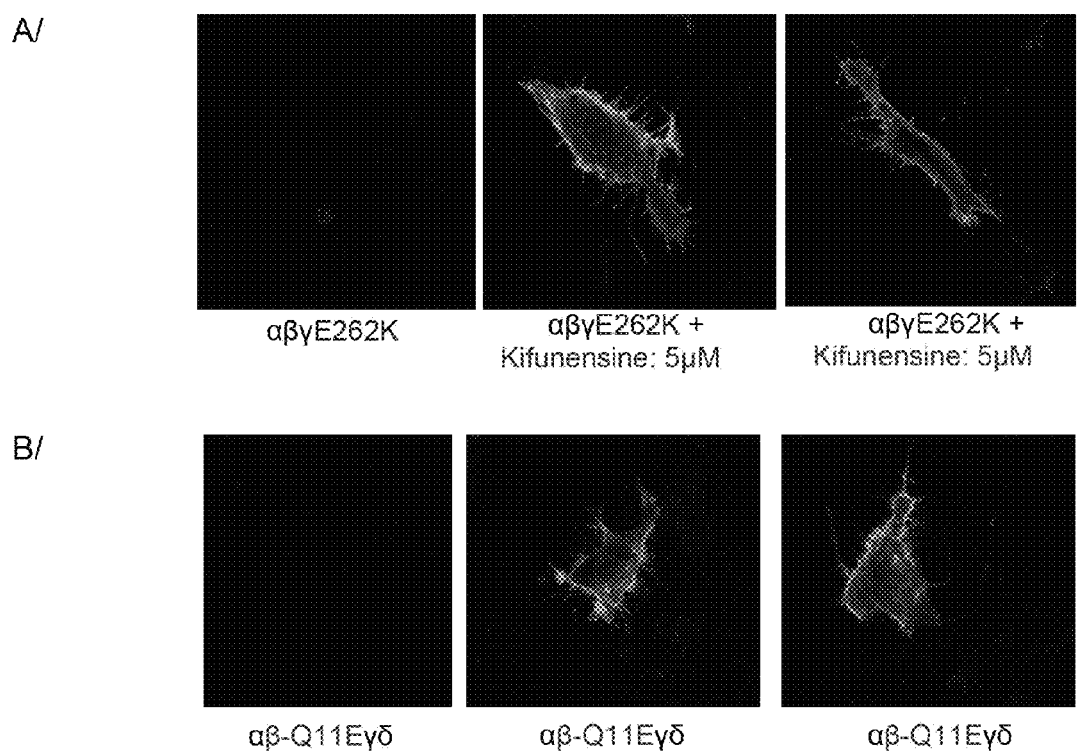

FIG. 13: A/Immunohistochemical labelling of δ-sarcoglycan in cells quadritransfected with the three α-, β- and γ-sarcoglycans and mutant E262K δ-sarcoglycan with or without kifunensin 5 μM.

B/Immunohistochemical labelling of β-sarcoglycan in cells quadritransfected with the three α-, γ- and δ-sarcoglycans and mutant Q11E β-sarcoglycan with or without kifunensin 5 μM.

DETAILED DESCRIPTION

I) Material and Methods

1—Production of Sgca$^{77C/77C}$ Mice

A 1075 bp DNA fragment carrying exons 2 and 3 of the Sgca gene obtained by BamHI-SfiI digestion of a phage containing the Sgca gene was amplified by PCR and then inserted into the pSP72 plasmid vector (Promega). The H77C mutation was generated in exon 3 by site-directed mutagenesis using the following primers: 5'-GCCCAGGTGGCTG TGCTACACACAGCGCA-3' (SEQ ID 1) and 5'-TGCGCT-GTGTGTAGCACAGCCACCTGGGC-3' (SEQ ID 2). Presence of the point mutation was confirmed by sequencing. A 5' BglII-BamHI fragment of about 4 kb and a 2981 bp 3' SfiI-SpeI fragment were cloned into the pSP72 vector on each side of the mutant insert. The loxP-neo$^r$-loxP cassette from the pGEM-neo$^r$ vector was inserted via the EcoRV site in intron 3 and a thymidine kinase (TK) cassette was inserted downstream of the 3' fragment to produce the final recombinant vector.

The recombinant vector (25 μg) was linearised by SalI digestion and introduced into SE 129Sv cells by electroporation. The DNA of G418 resistant colonies was then isolated and analysed by PCR or Southern blot to check for recombination events. Two distinct recombinant clones (IB4 and VII- ICII) were injected into C57B1/6 blastocysts and chimera mice were generated. Chimeric males were crossed with C57B1/6 females to produce heterozygous mice. The neo$^r$ cassette was eliminated by crosses with the deleter strain (15). The resulting mice in which the neo$^r$ cassette had been excised were then bred to produce homozygous mutant mice.

Genotyping was performed by PCR on tail DNA extracted using the Qiagen DNeasy Tissue Kit, using the upstream primers a-sarcoQ5': 5'-TATAACCCTGGCTTCCTCTA-3' (SEQ ID 3) and testNeo 1 5'-CGAATTCGCCAATGACAA-GACGCT-3' (SEQ ID 4) and the downstream primer a-sarcoQ3' 5'-TAGTGGCTCATGCCTTTAAT-3' (SEQ ID 5), generating a 639 bp product for the mutant allele carrying the neo$^r$ cassette and a 484 bp product for the wild-type allele, using the following PCR conditions: 94° C. for 3 minutes, then 30 cycles consisting of 94° C. for 30 s, 61° C. for 40 s and 72° C. for 1 minute, and then 3 minutes at 72° C. After excision of the neo$^r$ cassette, genotyping was performed with the a-sarcoQ5' (SEQ ID 3) and a-sarcoQ3' (SEQ ID 5) primers, generating a 575 bp product for the mutant allele.

To check that the H77C mutation was present in the Sgca gene of the model, a PCR was performed on tail DNA with primers KIgenoseq2.s 5'-TGTGTTTGGGACTTATGGGG-3' (SEQ ID 6) and KIgenoseq2.as 5'-CAATCAGCAGCAG-CAGCCTC-3' (SEQ ID 7) generating a 659 bp PCR product that was then sequenced.

2—Histology and Immunohistochemistry

8 μm cross-sections from frozen muscle were stained using haematoxylin and eosin (H&E). Cross-sections from mice injected with Evans blue were revealed by fluorescent excitation at 633 nm.

Cross-sections were dried, then rehydrated in PBS or fixed cells were treated for 20 min with 1% triton in PBS, then incubated for 30 min at room temperature (RT) in PBS containing 15% foetal calf serum. Cross-sections were incubated with polyclonal anti-sarcoglycan antibodies (α-sarcoglycan: dilution 1/1000, targeting amino acids 366-379 of human α-sarcoglycan; β-sarcoglycan: dilution 1/20, NCL-b-SARC (Novocastra); γ-sarcoglycan: dilution 1/20, NCL-g-SARC (Novocastra); dystrophin: dilution 1/20, NCL-DYS2 (Novocastra); and calreticulin: dilution 1/70, ab4109 (Abcam)) for 1 to 2 hours at RT then rinsed 3 times in PBS. Primary antibodies were revealed after 1 hour incubation at RT with secondary antibodies conjugated with fluorochromes Alexa488 (A-11032, Molecular Probes) or Alexa594 (A-11037, Molecular Probes), diluted 1:1000 in PBS. Cross-sections were then rinsed three times in PBS, mounted with fluoromount-G (Southern Biotech 0100-01) and then observed with a confocal microscope (Leica). Immunohistochemical analysis of human biopsy specimens was performed as described in Hackman et al. (9).

Plasmids pAAV_C5-12_α-SG, pcDNA3_α-SG, pcDNA3_β-SG, pcDNA3_γ-SG and pcDNA3_δ-SG were produced by PCRs on skeletal muscle cDNA and clones using the TOPO TA cloning kit (Invitrogen). Sarcoglycans were then subcloned into the pcDNA3 plasmid (Invitrogen) or pAAV_C5-12_MCS(3). Plasmids pcDNA3_α-SG-R77C and pAAV_C5-12_α-SG-R77C were obtained from pcDNA3-α-SG or pAAV_C5-12_α-SG by site-directed mutagenesis using the Quickchange site-directed mutagenesis kit (Stratagene) and the following primer: 5'-GCCCCG-GTGGCTCTGCTACACCCAGCGC-3' (SEQ ID 8). The constructions were checked by enzymatic digestion and sequencing.

The adenovirus-free AAV 2/1 viral preparations were produced by introducing recombinant AAV2-ITR genomes into AAV1 capsids using the tritransfection protocol (2). Viral genomes were quantified by dot blot in comparison with a series of standard plasmid dilutions.

4—Cell Culture

NIH3T3 or 911 cells were grown in Dulbecco's Modified Eagle Medium supplemented with glutamine, gentamicin and 10% foetal calf serum. Cells were transfected using 6 μA Fugene (ROCHE) per 1 μg plasmid. 0.5 μg of each plasmid (α-SG or α-SG-R77C and β-SG, γ-SG, δ-SG) was used per well in 6-well dishes. For treatment by inhibitors, 43 hours after transfection cells were incubated for 5 hours with either the mannosidase inhibitor (kifunensin 5 μM, VWR) or the proteasome inhibitor (MG132 5 μM diluted in DMSO, Sigma). Cells were then rinsed in PBS and fixed with 3.7% formaldehyde in PBS for 15 min at RT, and rinsed three more times in PBS before immunohistochemical labelling.

5—In Vivo Experiments

Sgca$^{77C/77C}$ mice were exercised for 30 minutes per day on a treadmill (Columbus treadmill instrument Exer 6M) on 3 consecutive days. Mice were placed on a treadmill with a downward incline of 15° and the speed was set at 10 meters per minute. At the end of the 3 days, mice were injected intraperitoneally with Evans blue dye (0.5 mg/g). Mice were sacrificed the day following injection and the deltoid, psoas, gastrocnemius, gluteus, extensor digitorum longus and quadriceps muscles were dissected and frozen rapidly in isopentane chilled with liquid nitrogen.

The rAAV2/1 viral preparations were injected ($10^{10}$ viral genomes (vg) in 30 μl total volume) in the left tibialis anterior muscle of Sgca−/− mice. On days 20, 22, 25 and 27 after injection, 10 μM kifunensin or 20 μM MG132 were injected into the muscle (i.e. either twice or 4 times the concentrations used in vitro to take into account diffusion within the muscle). One day prior to sacrifice (day 27), mice were injected intraperitoneally with Evans blue dye. Both left and right tibialis muscles were dissected and frozen rapidly in isopentane chilled with liquid nitrogen.

II) Results

1—Mutant R77C α-Sarcoglycan is Absent from the Membrane in Humans.

Figure 1:
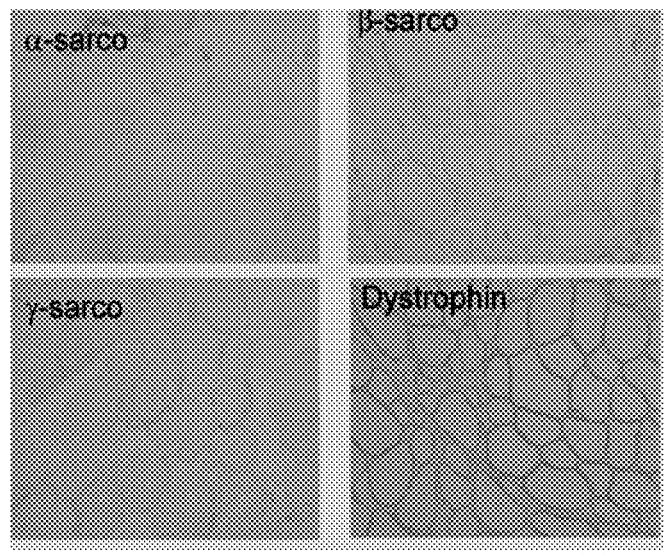
FIG. 1: Immunohistochemical labelling of α-, β-, γ-sarcoglycans and dystrophin on a muscle biopsy specimen from a patient carrying the α-sarcoglycan R77C mutation.

The presence of mutation R77C in α-sarcoglycan in humans leads to destabilisation of the sarcoglycan complex, as shown by immunohistochemical labelling using antibodies against various distinct proteins of the complex (FIG. 1).

2—In the Mouse, the Presence of a Cysteine in Position 77 does not Prevent α-Sarcoglycan Membrane Targeting and does not Result in a Pathological Condition.

Figure 2:
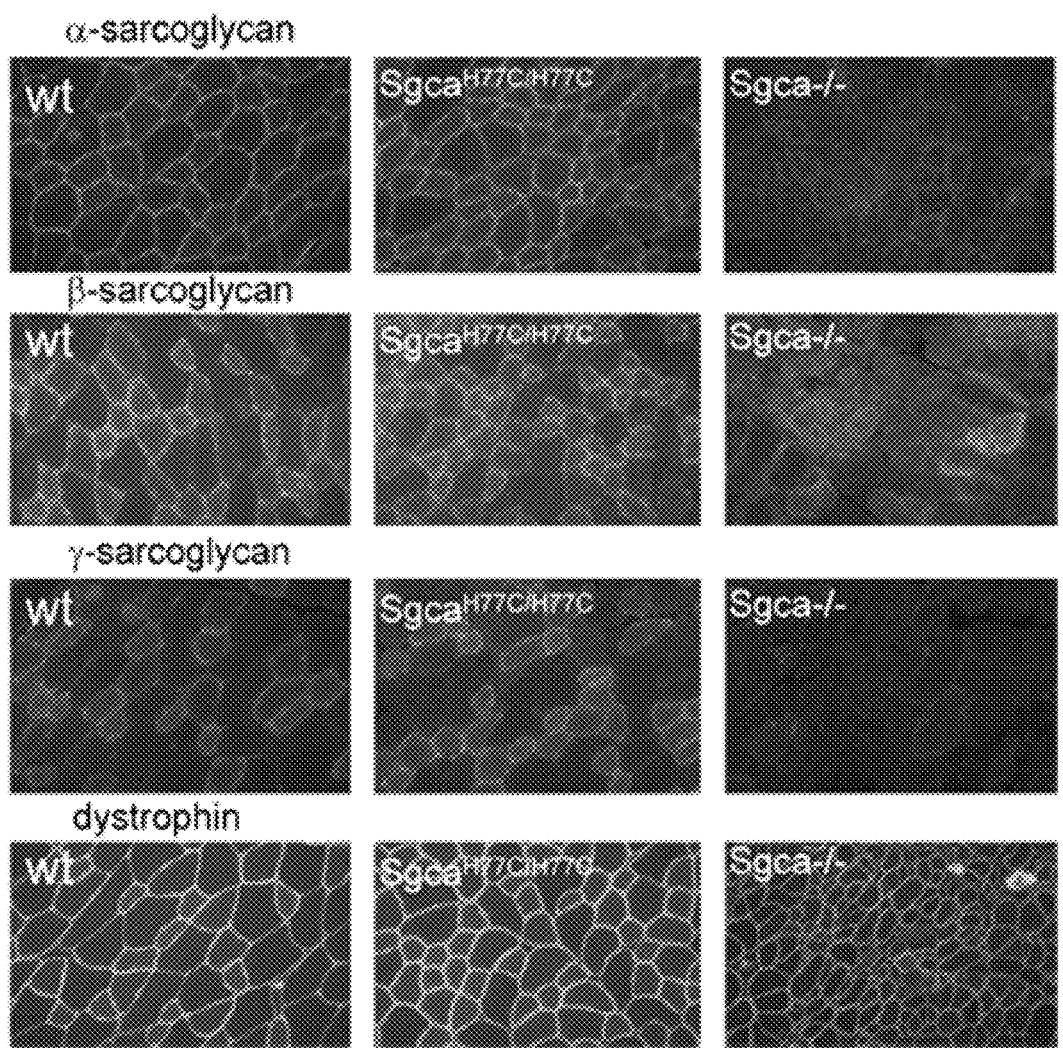
FIG. 2: Immunohistochemical labelling of α-, β-, γ-sarcoglycans and dystrophin in the mouse, in normal (WT), Sgca$^{77C/77C}$ and Sgca–/– muscles.

In order to investigate the reasons for complex destabilisation, we produced, by homologous recombination, an animal model (Sgca$^{77C/77C}$) bearing a cysteine in position 77. It should be noted that normal mice bear a histidine residue at this position and not an arginine residue. Immunohistochemical analysis of muscles from these mice using antibodies against various DGC complex proteins demonstrated that this mutation did not prevent α-sarcoglycan membrane targeting or assembly of the sarcoglycan complex (FIG. 2). Tissue cross-sections from wild-type and α-sarcoglycan deficient (Sgca−/−, 8) mice were used as controls.

Figure 3:
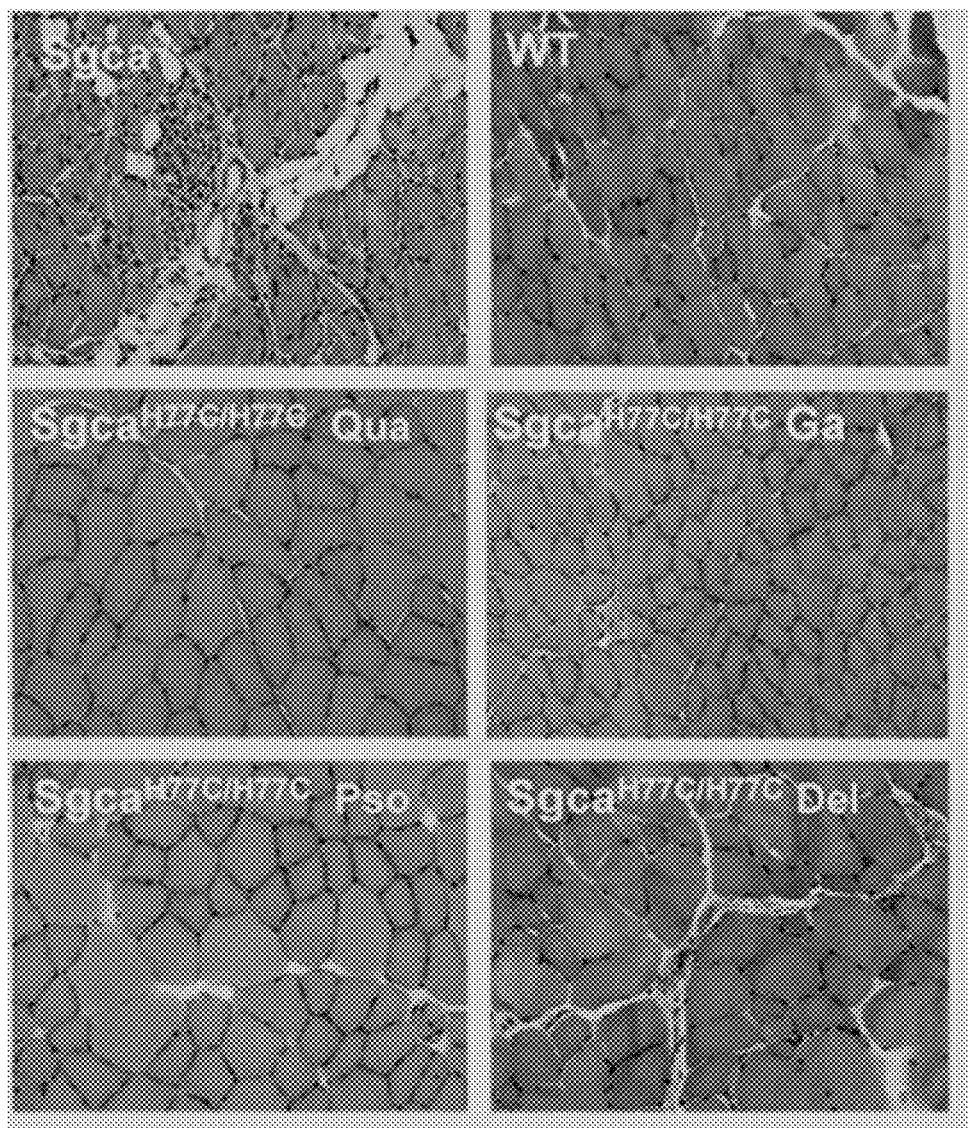
FIG. 3: Histology of Sgca–/–, WT and Sgca$^{77C/77C}$ muscles (Qua=quadriceps, Ga=gastrocnemius, Pso=psoas, Del=deltoid).

The histology of the deltoid, psoas, gastrocnemius and quadriceps muscles from 3 to 6 month old SgCa$^{77C/77C}$ mice was examined by haematoxylin/eosin staining and compared to Sgca−/− mouse tissue. Although the latter display the signs of severe dystrophy, no anomalies were detected in Sgca$^{77C/77C}$ muscles (FIG. 3).

Figure 4:
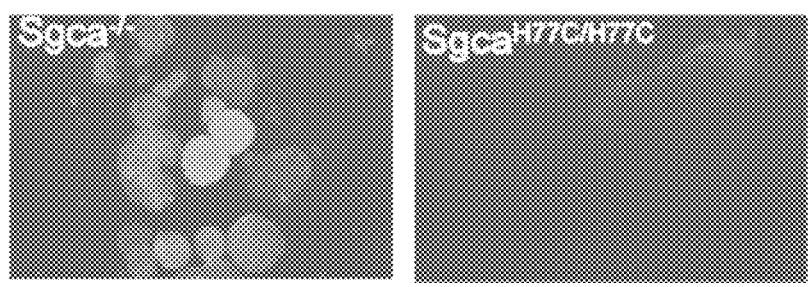
FIG. 4: Detection of necrotic cells using Evans blue staining in Sgca–/– and Sgca$^{77C/77C}$ muscles.

The absence of muscle anomalies was confirmed by functional analysis. SgCa$^{77C/77C}$ mice were subjected to exercise enhancing eccentric muscle contractility and then injected intraperitoneally with Evans blue dye, a dye that specifically stains necrotic cells. No Evans blue dye penetration was observed in the muscles of SgCa$^{77C/77C}$ mice (FIG. 4).

Figure 5:
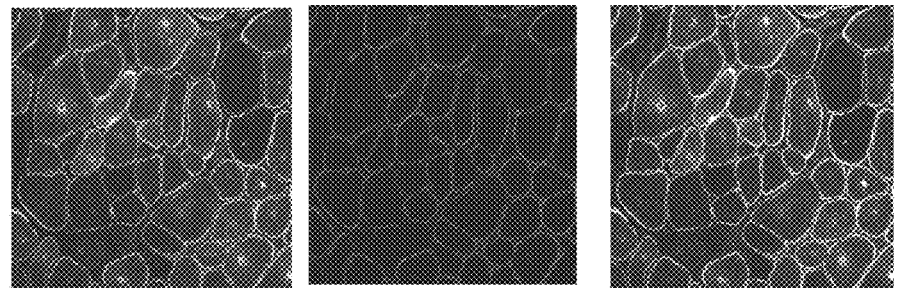
FIG. 5: Immunohistochemical labelling of α-sarcoglycan and β-sarcoglycan in Sgca–/– muscles after injection of AAV-humanSgca77C. Left: α-sarcoglycan; centre: β-sarcoglycan; right: both α- and β-sarcoglycans.
Figure 6:
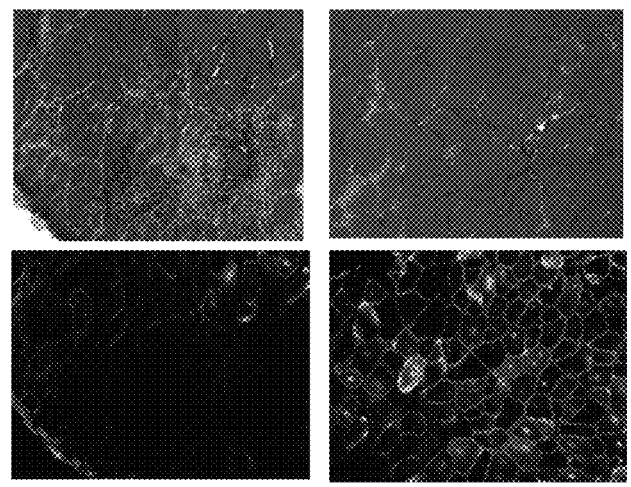
FIG. 6: Histology of Sgca–/– muscles after injection of AAV-Sgca77C (left: non-transduced area; right: transduced area).

To determine whether the differences observed between mice and humans when a cysteine residue is present in position 77 were related to the intrinsic properties of the human protein, we performed gene transfer experiments in muscles of α-sarcoglycan deficient mice using a viral vector derived from the adeno-associated virus (AAV) carrying the human α-sarcoglycan gene mutated in position 77. Analysis of these injected muscles demonstrated that the mutant protein is localised in the membrane, although some protein is retained in the reticulum, that the sarcoglycan complex assembles and that the pathological phenotype is corrected (FIGS. 5 and 6). It should be noted, as seen in FIG. 5, that α-sarcoglycan accumulates in the perinuclear space in some cells.

3—The Mutation Causes α-Sarcoglycan Retention and its Degradation by the Proteasome.

Figure 7:
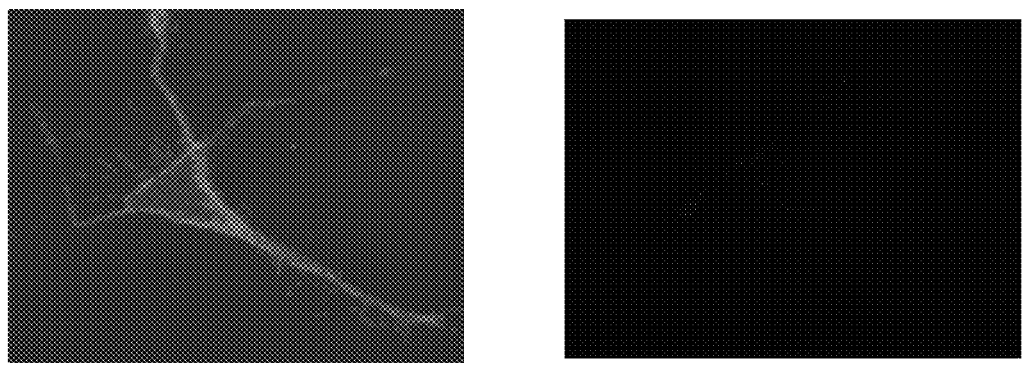
FIG. 7: Immunohistochemical labelling of α-sarcoglycan in non-permeabilised quadritransfected cells. Left: quadritransfection with normal α-sarcoglycan; right: with mutant α-sarcoglycan.

We have established a cellular model reproducing the phenomena observed in humans by quadritransfecting plasmids coding the four different sarcoglycans. In this model, the complex assembles correctly at the membrane when normal α-sarcoglycan is co-transfected together with the three other sarcoglycans. However, correct assembly is not observed at the membrane when the R77C α-sarcoglycan is transfected. This was demonstrated by immunohistochemical labelling using an antibody against the extracellular segment of α-sarcoglycan on non-permeabilised cells (FIG. 7).

Figure 8:
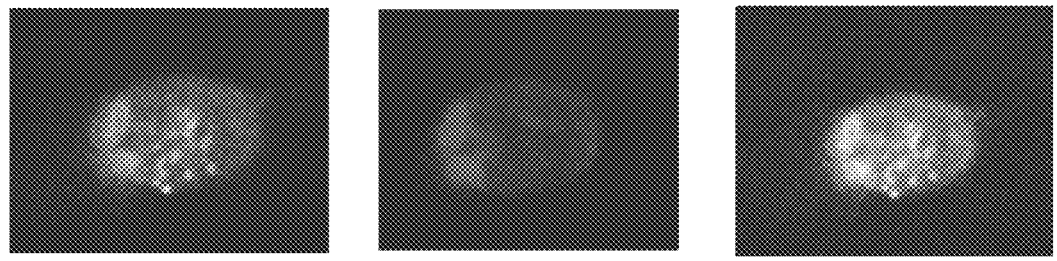
FIG. 8: Immunohistochemical labelling of α-sarcoglycan (left) and calreticulin (centre). Right: overlay of both stains.

Double-labelling of α-sarcoglycan and an endoplasmic reticulum marker (calreticulum) in permeabilised cells showed that mutant protein was retained in the secretion pathway (FIG. 8).

Figure 9:
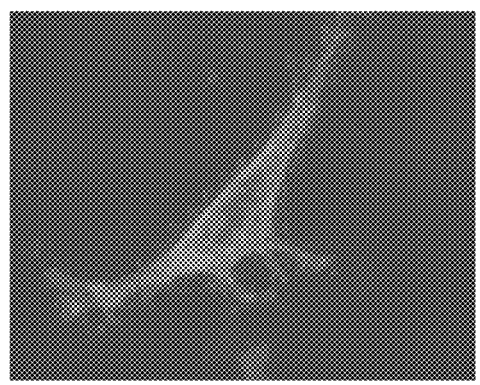
FIG. 9: Immunohistochemical labelling of α-sarcoglycan in quadritransfected cells with mutant α-sarcoglycan in the presence of MG132.

We postulated that mutant α-sarcoglycan was recognised as abnormal by the protein quality control system of the reticulum and then degraded by the proteasome. This was confirmed by use of the proteasome inhibitor MG132 which restored membrane targeting (FIG. 9).

Figure 10:
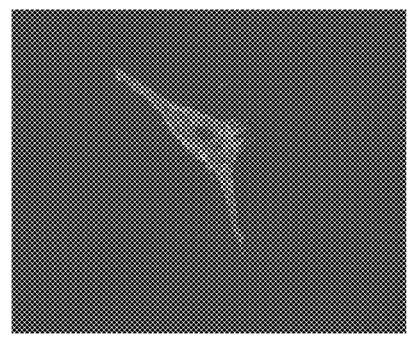
FIG. 10: Immunohistochemical labelling of α-sarcoglycan in quadritransfected cells with mutant α-sarcoglycan in the presence of kifunensin.

The protein quality control system of the reticulum leads to degradation of incorrectly folded proteins. The mannosidase I enzyme plays an important role in this process by modifying the oligosaccharide chains of glycosylated proteins such as sarcoglycans. Bearing in mind these facts and our results, we postulated that use of an inhibitor of this enzyme might restore membrane targeting of the mutant α-sarcoglycan protein. This hypothesis was validated in our cellular model in cells quadritransfected with mutant α-sarcoglycan and then treated by kifunensin (FIG. 10).

Figure 11:
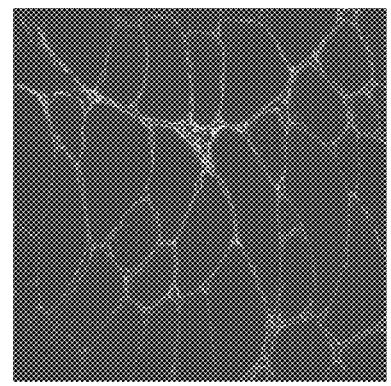
FIG. 11: Immunohistochemical labelling of α-sarcoglycan showing the absence of aggregates after a week of treatment with kifunensin in mouse Sgca–/– muscle injected with mutant α-sarcoglycan.

The differences observed between humans and mice meant that we did not have an in vivo mouse model corresponding to the molecular events observed in humans. However, a decrease in the partial retention of the mutant protein after gene transfer would suggest that mannosidase I inhibition could have a beneficial effect on α-sarcoglycan membrane targeting. To determine whether use of the inhibitor might be effective in vivo, Sgca−/− mice first received an injection of the AAV-SGCA77C vector and then (15 days later) received three intramuscular injections of the inhibitor over a one week period. Muscles that were injected with the inhibitor displayed a nearly complete absence of intracellular aggregates, and notably an absence of accumulation in the perinuclear space. These results validated our working hypothesis (FIG. 11).

The same convincing results were obtained with kifunensin for two other point mutations on two other sub-units from the sarcoglycan complex: mutation E262K on sub-unit δ (FIG. 13A) and mutation Q11E on sub-unit β (FIG. 13B).

5—Restoration by 1-Deoxymannojirimycin (dMJ)

Experiments similar to those performed with kifunensin on mutant R77C α-sarcoglycan were performed using 1-deoxymannojirimycin (dMJ), another class I mannosidase inhibitor. Results are shown in FIG. 12A and demonstrate the efficacy of this substance for restoring membrane targeting of mutant α-sarcoglycan (R77C mutation).

Figure 12:
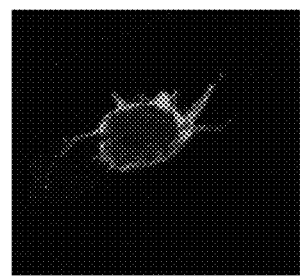
FIG. 12: A/Immunohistochemical labelling of α-sarcoglycan in cells quadritransfected with the three β-, γ- and δ-sarcoglycans and normal α-sarcoglycan (left), or mutant R77C α-sarcoglycan without (centre) or with (right) 100 μM 1-deoxymannojirimycin (dMJ).
Figure 12:
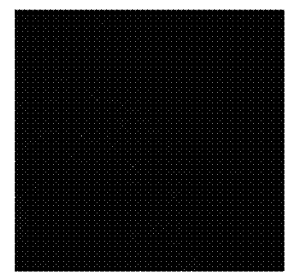
Figure 12:
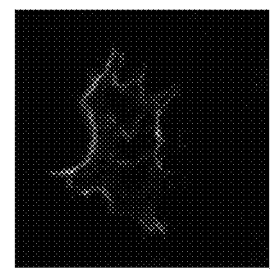
Figure 12:
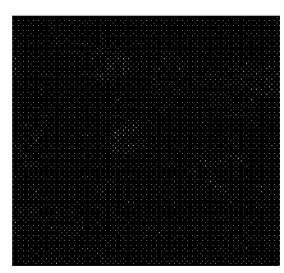
Figure 12:
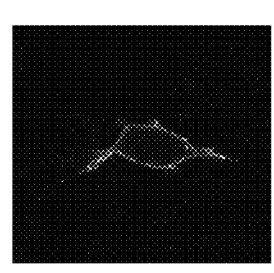
Figure 12:
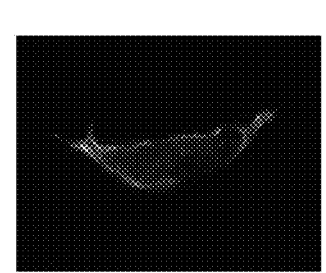
Figure 12:
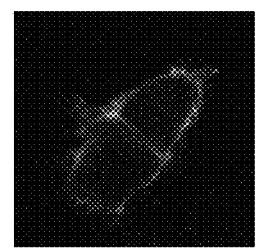
Figure 12:
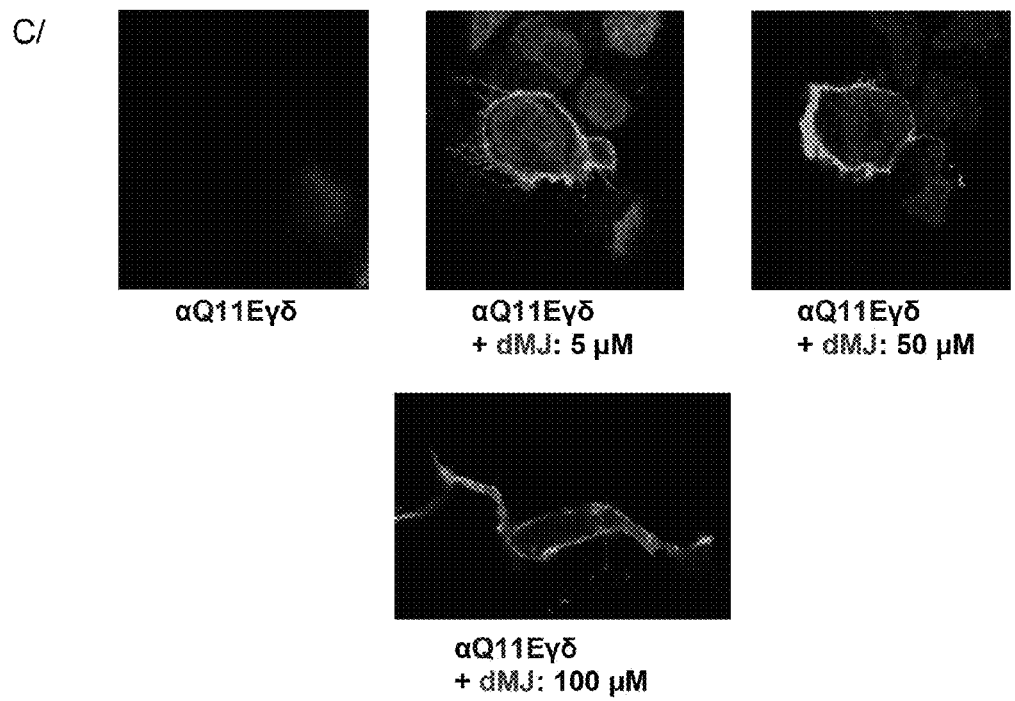

In addition, similar experiments confirmed our working hypothesis for other mutations on other sub-units of the sarcoglycan complex: mutation E262K on sub-unit δ (FIG. 12B) and mutation Q11E on sub-unit β (FIG. 12C).

To conclude, we have shown that mutant α-sarcoglycan bearing a cysteine in position 77 is managed quite differently in mouse and human cells, and that this mutant protein is functional if it is located correctly and can remedy the pathological condition related to sarcoglycan deficiency. We have demonstrated, in a cellular model, that mannosidase I inhibition prevents degradation of mutant sarcoglycan and restores membrane targeting. Use of this substance in vivo also seems to produce the same results.

REFERENCES

1—Allamand, V., K. M. Donahue, V. Straub, R. L. Davisson, B. L. Davidson, and K. P. Campbell. 2000. Early adenovirus-mediated gene transfer effectively prevents muscular dystrophy in alpha-sarcoglycan-deficient mice. *Gene Ther.* 7:1385-91.

2—Bartoli, M., J. Poupiot, A. Goyenvalle, N. Perez, L. Garcia, O. Danos, and I. Richard. 2006a. Non-invasive Monitoring of Therapeutic Gene Transfer in Animal Models of Muscular Dystrophies. *Gene Therapy.* 13:20-8.

3—Bartoli, M., C. Roudaut, S. Martin, F. Fougerousse, L. Suel, J. Poupiot, E. Gicquel, F. Noulet, O. Danos, and I. Richard. 2006b. Safety and efficacy of AAV-mediated calpain 3 gene transfer in a mouse model of limb-girdle muscular dystrophy type 2A. *Mol Ther.* 13:250-9.

4—Bonnemann, C. G., J. Wong, K. J. Jones, H. G. Lidov, C. A. Feener, F. Shapiro, B. T. Darras, L. M. Kunkel, and K. N. North. 2002. Primary gamma-sarcoglycanopathy (LGMD 2C): broadening of the mutational spectrum guided by the immunohistochemical profile. *Neuromuscul Disord.* 12:273-80.

5—Carrie, A., F. Piccolo, F. Leturcq, C. de Toma, K. Azibi, C. Beldjord, J. M. Vallat, L. Merlini, T. Voit, C. Sewry, J. A. Urtizberea, N. Romero, F. M. Tome, M. Fardeau, Y. Sunada, K. P. Campbell, J. C. Kaplan, and M. Jeanpierre. 1997. Mutational diversity and hot spots in the alpha-sarcoglycan gene in autosomal recessive muscular dystrophy (LGMD2D). *J Med Genet.* 34:470-5.

6—Chan, Y. M., C. G. Bonnemann, H. G. Lidov, and L. M. Kunkel. 1998. Molecular organization of sarcoglycan complex in mouse myotubes in culture. *J Cell Biol.* 143: 2033-44.

7—Dressman, D., K. Araishi, M. Imamura, T. Sasaoka, L. A. Liu, E. Engvall, and E. P. Hoffman. 2002. Delivery of alpha- and beta-sarcoglycan by recombinant adeno-associated virus: efficient rescue of muscle, but differential toxicity. *Hum Gene Ther.* 13:1631-46.

8—Duclos, F., V. Straub, S. A. Moore, D. P. Venzke, R. F. Hrstka, R. H. Crosbie, M. Durbeej, C. S. Lebakken, A. J. Ettinger, J. van der Meulen, K. H. Holt, L. E. Lim, J. R. Sanes, B. L. Davidson, J. A. Faulkner, R. Williamson, and K. P. Campbell. 1998. Progressive muscular dystrophy in alpha-sarcoglycan-deficient mice. *J Cell Biol.* 142:1461-71.

9—Hackman, P., V. Juvonen, J. Sarparanta, M. Penttinen, T. Aarimaa, M. Uusitalo, M. Auranen, H. Pihko, R. Alen, M. Junes, T. Lonnqvist, H. Kalimo, and B. Udd. 2004. Enrichment of the R77C alpha-sarcoglycan gene mutation in Finnish LGMD2D patients. *Muscle Nerve.*

10—Lapidos, K. A., R. Kakkar, and E. M. McNally. 2004. The dystrophin glycoprotein complex: signaling strength and integrity for the sarcolemma. *Circ Res.* 94:1023-31.

11—Nigro, V. 2003. Molecular bases of autosomal recessive limb-girdle muscular dystrophies. *Acta Myol.* 22:35-42.

12—Ozawa, E., Y. Mizuno, Y. Hagiwara, T. Sasaoka, and M. Yoshida. 2005. Molecular and cell biology of the sarcoglycan complex. *Muscle Nerve.*

13—Piccolo, F., M. Jeanpierre, F. Leturcq, C. Dode, K. Azibi, A. Toutain, L. Merlini, L. Jarre, C. Navarro, R. Krishnamoorthy, F. M. Tome, J. A. Urtizberea, J. S. Beckmann, K. P. Campbell, and J. C. Kaplan. 1996. A founder mutation in the gamma-sarcoglycan gene of gypsies possibly predating their migration out of India. *Hum Mol Genet.* 5:2019-22.

14—Sampaolesi, M., Y. Torrente, A. Innocenzi, R. Tonlorenzi, G. D'Antona, M. A. Pellegrino, R. Barresi, N. Bresolin, M. G. De Angelis, K. P. Campbell, R. Bottinelli, and G. Cossu. 2003. Cell therapy of alpha-sarcoglycan null dystrophic mice through intra-arterial delivery of mesoangioblasts. *Science.* 301:487-92.

15—Schwenk, F., U. Baron, and K. Rajewsky. 1995. A cre-transgenic mouse strain for the ubiquitous deletion of loxP-flanked gene segments including deletion in germ cells. *Nucleic Acids Res.* 23:5080-1.

16—Shi, W., Z. Chen, J. Schottenfeld, R. C. Stahl, L. M. Kunkel, and Y. M. Chan. 2004. Specific assembly pathway of sarcoglycans is dependent on beta- and delta-sarcoglycan. *Muscle Nerve.* 29:409-19.

17—Vainzof, M., M. R. Passos-Bueno, M. Canovas, E. S. Moreira, R. C. Pavanello, S. K. Marie, L. V. Anderson, C. G. Bonnemann, E. M. McNally, V. Nigro, L. M. Kunkel, and M. Zatz. 1996. The sarcoglycan complex in the six autosomal recessive limb-girdle muscular dystrophies. *Hum Mol Genet.* 5:1963-9.

The invention claimed is:

1. A method of treating a sarcoglycanopathy comprising administering to a subject in need of such treatment a therapeutically effective amount of a class I α-mannosidase inhibitor.

2. A method according to claim 1 wherein said inhibitor comprises at least one of a structural analog of kifunensin and a structural analog of 1-deoxymannojirimycin.

3. A method according to claim 1, wherein the sarcoglycanopathy comprises a pathological degradation of a sarcoglycan in cells of the subject.

4. A method according to claim 1, wherein the sarcoglycanopathy comprises a pathological reduction in the presence of one or more sarcoglycans at the cellular membrane of a cell of the subject.

5. A method according to claim 1, wherein the sarcoglycanopathy comprises at least one sarcoglycan bearing at least one of the amino acid substitutions depicted in Table I.

6. A method according to claim 5, wherein the amino acid substitution is at least one of an R77C substitution on human a-sarcoglycan, an E262K substitution on human δ-sarcoglycan, and a Q11E substitution on human β-sarcoglycan.

7. A method according to claim 5, wherein the amino acid substitution is at least one of a T151R substitution on human β-sarcoglycan, a C283Y substitution on human γ-sarcoglycan, and an L194S substitution on human γ-sarcoglycan.

8. A method according to claim 1 wherein said inhibitor comprises at least one of kifunensin, 1-deoxymannojirimycin, a structural analog of kifunensin, and a structural analog of 1-deoxymannojirimycin, and wherein the sarcoglycanopathy comprises a pathological degradation of a sarcoglycan in cells of the subject.

9. A method according to claim 1 wherein said inhibitor comprises at least one of kifunensin, 1-deoxymannojirimycin, a structural analog of kifunensin, and a structural analog of 1-deoxymannojirimycin, and wherein the sarcoglycanopathy comprises at least one sarcoglycan bearing at least one of the amino acid substitutions depicted in Table I.

10. A method according to claim 1 wherein said inhibitor comprises at least one of kifunensin, 1-deoxymannojirimycin, a structural analog of kifunensin, and a structural analog of 1-deoxymannojirimycin, and wherein the amino acid substitution is at least one of an R77C substitution on human α-sarcoglycan, an E262K substitution on human δ-sarcoglycan, and a Q11E substitution on human β-sarcoglycan.

11. A method according to claim 1 wherein said inhibitor comprises at least one of kifunensin, 1-deoxymannojirimycin, a structural analog of kifunensin, and a structural analog of 1-deoxymannojirimycin, and wherein the amino acid substitution is at least one of a T151R substitution on human β-sarcoglycan, a C283Y substitution on human γ-sarcoglycan, and an L194S substitution on human γ-sarcoglycan.

12. A method according to claim 1 wherein said inhibitor comprises at least one of kifunensin, 1-deoxymannojirimycin, a structural analog of kifunensin, and a structural analog of 1-deoxymannojirimycin, and wherein the sarcoglycanopathy comprises a pathological reduction in the presence of one or more sarcoglycans at the cellular membrane of a cell of the subject.

13. A method according to claim 5, wherein the sarcoglycanopathy comprises at least one of a pathological degradation of a sarcoglycan in cells of the subject and a pathological reduction in the presence of one or more sarcoglycans at the cellular membrane of a cell of the subject.

14. A method according to claim 6, wherein the sarcoglycanopathy comprises at least one of a pathological degradation of a sarcoglycan in cells of the subject and a pathological reduction in the presence of one or more sarcoglycans at the cellular membrane of a cell of the subject.

15. A method according to claim 7, wherein the sarcoglycanopathy comprises at least one of a pathological degradation of a sarcoglycan in cells of the subject and a pathological reduction in the presence of one or more sarcoglycans at the cellular membrane of a cell of the subject.

16. A method according to claim 9, wherein the sarcoglycanopathy comprises at least one of a pathological degradation of a sarcoglycan in cells of the subject and a pathological reduction in the presence of one or more sarcoglycans at the cellular membrane of a cell of the subject.

17. A method according to claim 10, wherein the sarcoglycanopathy comprises at least one of a pathological degradation of a sarcoglycan in cells of the subject and a pathological reduction in the presence of one or more sarcoglycans at the cellular membrane of a cell of the subject.

18. A method according to claim 11, wherein the sarcoglycanopathy comprises at least one of a pathological degradation of a sarcoglycan in cells of the subject and a pathological reduction in the presence of one or more sarcoglycans at the cellular membrane of a cell of the subject.

* * * * *